United States Patent
Choi et al.

(10) Patent No.: US 10,154,796 B2
(45) Date of Patent: *Dec. 18, 2018

(54) THREE-DIMENSIONAL ELECTRICAL IMPEDANCE TOMOGRAPHY SYSTEM

(71) Applicant: National Chiao Tung University, Hsinchu (TW)

(72) Inventors: Charles Tak Ming Choi, Hsinchu (TW); Shu-Hai Sun, Hsinchu (TW)

(73) Assignee: National Chiao Tung University, Hsinchu (TW)

( * ) Notice: Subject to any disclaimer, the term of this patent is extended or adjusted under 35 U.S.C. 154(b) by 0 days.

This patent is subject to a terminal disclaimer.

(21) Appl. No.: 15/945,359

(22) Filed: Apr. 4, 2018

(65) Prior Publication Data

US 2018/0220922 A1    Aug. 9, 2018

Related U.S. Application Data

(63) Continuation of application No. 13/729,811, filed on Dec. 28, 2012, now Pat. No. 9,962,105.

(30) Foreign Application Priority Data

Dec. 30, 2011    (TW) .............................. 100149801 A

(51) Int. Cl.
*A61B 5/04* (2006.01)
*A61B 5/05* (2006.01)
(Continued)

(52) U.S. Cl.
CPC .............. *A61B 5/0536* (2013.01); *A61B 5/12* (2013.01); *A61B 5/407* (2013.01); *A61B 5/4064* (2013.01); *A61B 5/6814* (2013.01); *A61B 5/6822* (2013.01); *A61B 5/6823* (2013.01); *A61B 5/6868* (2013.01); *A61B 5/7225* (2013.01); *A61B 5/7278* (2013.01)

(58) Field of Classification Search
CPC ......... A61B 5/053; A61B 5/12; A61B 5/4064; A61B 5/407; A61B 5/6814; A61B 5/6822; A61B 5/6823; A61B 5/6868
USPC ................................ 600/372, 407, 533, 547
See application file for complete search history.

(56) References Cited

U.S. PATENT DOCUMENTS 6,725,087 B1    4/2004    Rubinsky et al.
7,660,617 B2    2/2010    Davis
(Continued)

*Primary Examiner* — Joseph Stoklosa
*Assistant Examiner* — Brian M Antiskay
(74) *Attorney, Agent, or Firm* — Mintz Levin Cohn Ferris Glovsky and Popeo, P.C.; Peter F. Corless; Steven M. Jensen

(57) ABSTRACT

The present disclosure provides a method for improving imaging resolution of electrical impedance tomography (EIT). More specifically, the present disclosure forms virtual electrode(s) using an electric current steering technique, which is used to improve imaging resolution of an EIT system without physically increasing a number of conducting electrodes. The EIT system of the present disclosure may includes a plurality of conducting electrodes, at least one signal generator, at least one signal receiver and at least one electric current steering device. In other words, the present disclosure applies both the electric current steering technique and the virtual electrode technique to EIT. Consequently, imaging resolution of EIT can be improved without physically increasing the number of conducting electrodes.

20 Claims, 14 Drawing Sheets

(51) Int. Cl.
*A61B 5/053* (2006.01)
*A61B 5/12* (2006.01)
*A61B 5/00* (2006.01)

(56) References Cited

U.S. PATENT DOCUMENTS

| | | |
|---|---|---|
| 8,352,016 B2 | 1/2013 | Tanaka |
| 8,547,248 B2 | 10/2013 | Zdeblick et al. |
| 9,060,705 B2 | 6/2015 | Holzhacker et al. |
| 2001/0025178 A1 | 9/2001 | Mulier et al. |
| 2005/0107834 A1 | 5/2005 | Freeman et al. |
| 2006/0259098 A1 | 11/2006 | Erickson |
| 2010/0305675 A1 | 12/2010 | Laske et al. |
| 2011/0282414 A1 | 11/2011 | Kothandaraman et al. |

THREE-DIMENSIONAL ELECTRICAL IMPEDANCE TOMOGRAPHY SYSTEM

CROSS-REFERENCE TO RELATED APPLICATION(S)

This application is a divisional of copending application U.S. Ser. No. 13/729,811, filed on Dec. 28, 2012, which claims under 35 U.S.C. § 119(a) the benefit of Taiwanese Application No. 100149801, filed Dec. 30, 2011, the entire contents of which are incorporated herein by reference.

TECHNICAL FIELD

The present disclosure relates to a method for improving imaging resolution of electrical impedance tomography (EIT), and more specifically, to a method for improving imaging resolution of EIT with the electric current steering technique.

BACKGROUND

In recent years, the development of medical imaging technology enables the computed tomography (CT) scan, magnetic resonance imaging (MRI) and positron emission tomography (PET) to generate three-dimensional (3D) images.

Although the traditional scanning imaging techniques are able to produce a two-dimensional (2D) static-state image on an output film, a 3D image can be obtained through numerous image scans. 3D ultrasound imaging technology employs the similar technique. Further, in the diagnosis of certain parts of the body, such as brain, lung and chest, imaging technology with good resolution and reasonable prices is required to obtain high clarity of medical images for correctly diagnosing many diseases and conducting surgical treatment.

In addition, the electrical impedance tomography (EIT) technique has been widely applied to the medical imaging field. EIT has the advantages of non-invasion, low prices, no radiation hazards, and long-term monitoring, but has a drawback of low image resolution due to limited number of conducting electrodes. A common method for obtaining image data is to input an electric current to a pair of conducting electrodes and to measure potentials generated between other pair of conducting electrodes.

U.S. Pat. No. 6,725,087 discloses data acquisition, data processing and imaging components which are connected to a communication network. Thus data acquisition, data processing and image components within the communication network can be performed at different locations. Moreover, a journal paper titled "A Broadband High-frequency Electrical Impedance Tomography System for Breast Imaging," published in IEEE in February 2008, discloses that an EIT system is able to operate in a broadband range (10 kHz-10 MHz) and accuracy of the impedance measurement is improved by increasing frequency of an electric current, but image resolution of the EIT system is still unable to be improved effectively.

The current EIT techniques are shown in FIGS. 1A, 1B and 1C. Regarding an adjacent input configuration, as shown in FIG. 1, the surrounding of a tissue structure 100 is surrounded by a plurality of conducting electrodes 1-16 with electrical wires. An electric current source 104 may input an electric current into the tissue structure 100 through a conducting electrode 1 on the surrounding of the tissue structure 100, and there is an outflow of the electric current from a conducting electrode 3 on the surrounding of the tissue structure 100. A conductive target 102 generates certain electrical characteristics due to electric fields. Each conducting electrode has a corresponding equi-potential 108. A voltage measuring device 106 is used for measuring impedance within the tissue structure 100 and performing the reconstruction and display of the image of the conductive target 102 in the tissue structure 100. For example, the voltage measuring device 106 is connected to the conducting electrodes 6, 8, and measures impedance through the conducting electrodes 6 and 8. Typically, the voltage measuring device 106 is connected to some or all of the conducting electrodes 1-16 and measures impedance through these conducting electrodes. After the impedance measurements are completed, the reconstruction and display of the image of the conductive target 102 is performed. In addition, a cross input configuration method, as shown in FIG. 1B, is used for connecting an electric current source 104 with the conducting electrodes 1, 5 and measuring voltage through the conducting electrodes 2-4 and 6-16. The process of the cross input configuration method may be repeated. Moreover, an opposite input configuration method, as shown in FIG. 1C, is used for connecting the electric current source 104 with the conducting electrodes 1 and 9 and measures voltage through the conducting electrodes 2-8 and 10-16. The process of the opposite input configuration method may be repeated.

It can be seen that the current EIT techniques can be applied to imaging the internal structure of biological tissue or a body in great need of the lengthy measurement process. Even though the lengthy measurement process is performed, an image with high resolution still cannot be improved. However, resolution of an EIT image can be improved by dense allocation of conducting electrodes and physically increasing the number of conducting electrodes.

SUMMARY

In light of the foregoing drawbacks, an objective of the present disclosure is to provide a method for rapidly and effectively improving imaging resolution of electrical impedance tomography (EIT), thereby increasing accuracy of clinics and surgery, and overcoming the drawback of the current EIT techniques without sufficient imaging resolution.

In accordance with the above and other objectives, the present disclosure provides a method for improving imaging resolution of electrical impedance tomography (EIT) using a plurality of conducting electrodes on the surrounding of or inside a tissue structure, comprising the following steps of: inputting an electric current into the tissue structure through at least two of the plurality of conducting electrodes, and outputting the electric current from at least other one of the conducting electrodes; forming a virtual electrode between the at least two of the plurality of conducting electrodes by applying an electric current ratio to control the electric current using an electric current steering device; measuring an electric potential using at least two of the plurality of conducting electrodes, except these conducting electrodes for inputting and outputting the electric current, to obtain electric current and electric potential distributions corresponding to the plurality of conducting electrodes and the virtual electrode in the tissue structure; and performing an image conversion processing according to the electric current and electric potential distributions to profile an image of a specific region in the tissue structure.

Moreover, the present disclosure further provides a method for improving imaging resolution of electrical impedance tomography (EIT) using a plurality of conducting electrodes on the surrounding of or inside a tissue structure, comprising the following steps of: inputting an electric current into the tissue structure through at least one of the plurality of conducting electrodes, and outputting the electric current from at least other two of the plurality of conducting electrodes; forming a virtual electrode between the at least two of the plurality of conducting electrodes for applying an electric current ratio to control the electric current using an electric current steering device; measuring an electric potential using at least two of the plurality of conducting electrodes, except these conducting electrodes for inputting and outputting the electric current, to obtain electric current and electric potential distributions corresponding to the plurality of conducting electrodes and the virtual electrode in the tissue structure; and performing an image conversion processing according to the electric current and electric potential distributions to profile an image of a specific region in the tissue structure.

Furthermore, the present disclosure also provides a method for improving imaging resolution of electrical impedance tomography (EIT) using a plurality of signal electrodes on the surrounding of or inside a tissue structure, comprising the following steps of: inputting an electric current into the tissue structure through at least two of the plurality of conducting electrodes, and outputting the electric current from at least other two of the conducting electrodes; forming a virtual electrode between the at least two of the plurality of conducting electrodes for applying an electric current ratio to control the electric current using an electric current steering device; measuring an electric potential using at least two of the plurality of conducting electrodes, except these conducting electrodes for inputting and outputting the electric current, to obtain electric current and electric potential distributions corresponding to the plurality of conducting electrodes and the virtual electrodes in the tissue structure; and performing an image conversion processing according to the electric current and electric potential distributions to profile an image of a specific region in the tissue structure.

In addition, the present disclosure further provides a 3D EIT system, comprising: a plurality of conducting electrode devices, wherein each conducting device has a plurality of conducting electrodes; a tissue structure is located between the plurality of conducting electrode devices; an electric current is inputted into the tissue structure by at least two of the plurality of conducting electrode devices during performing EIT; an electric current ratio is adjusted and applied to control the electric current for profiling a 3D image of the tissue structure. The plurality of conducting electrode devices comprises the plurality of conducting electrodes in a ring manner.

Compared to prior art, the present disclosure not only increases a number of virtual electrodes using the electric current steering technique, but also applies the image conversion processing to profile an image of the tissue structure based on electric current and electric potential distributions, which are obtained by measuring electric current and electric potential through conducting electrodes and the number of virtual electrodes. A tissue structure image with high resolution can be obtained rapidly and effectively without physically increasing the number of conducting electrodes.

BRIEF DESCRIPTION OF THE DRAWINGS

The present disclosure can be more fully understood by reading the following detailed description of the preferred embodiments, with reference made to the accompanying drawings, wherein.

DETAILED DESCRIPTION

The present disclosure is described by the following specific embodiments. Those with ordinary skills in the arts can readily understand the other advantages and functions of the present disclosure after reading the disclosure of this specification. The present disclosure can also be implemented with different embodiments. Various details described in this specification can be modified based on different viewpoints and applications without departing from the scope of the present disclosure.

Figure 2A:
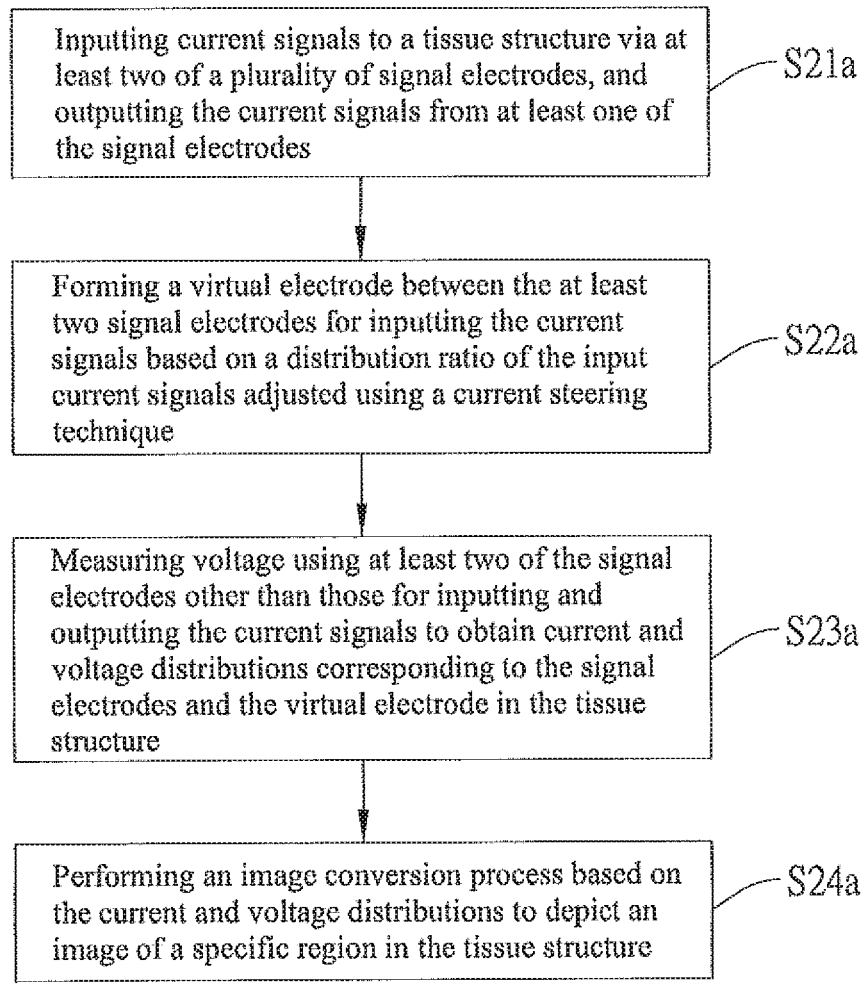
FIG. 2A is a flowchart illustrating a method for improving imaging resolution of EIT according to the first embodiment of the present disclosure.

The present disclosure provides a method for improving imaging resolution of electrical impedance tomography (EIT) using a plurality of conducing electrodes on the surrounding of or inside a tissue structure. FIG. 2A illustrates a flowchart of the method for improving imaging resolution of EIT according to the first embodiment of the present disclosure. A virtual electrode is formed between the plurality of conducting electrodes for inputting an electric current by an electric current steering device according to the first embodiment of the present disclosure, as shown in FIGS. 5A-5C.

As shown in FIG. 2A, the method begins with step S21a of inputting an electric current into the tissue structure 100 through at least two of the plurality of conducting electrodes, and outputting the electric current from at least other one of the plurality of conducting electrodes. In one embodiment of the present disclosure, the plurality of conducting electrodes are microelectrodes forming an electrode array. Moreover, the tissue structure 100 is a brain, a neck region or a chest region.

Figure 5A:
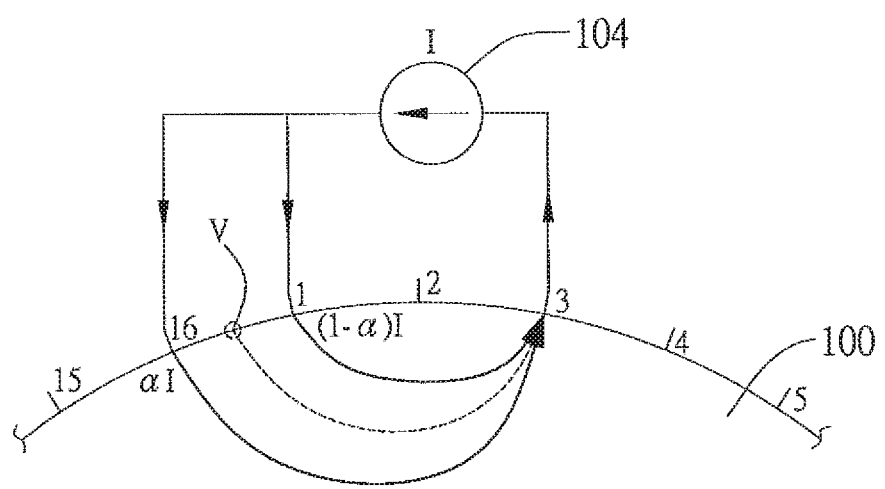
FIGS. 5A-5D are schematic diagrams illustrating a virtual electrode formed between the plurality of conducting electrodes for inputting an electric current by an electric current steering device according to the first embodiment of the present disclosure.
Figure 5B:
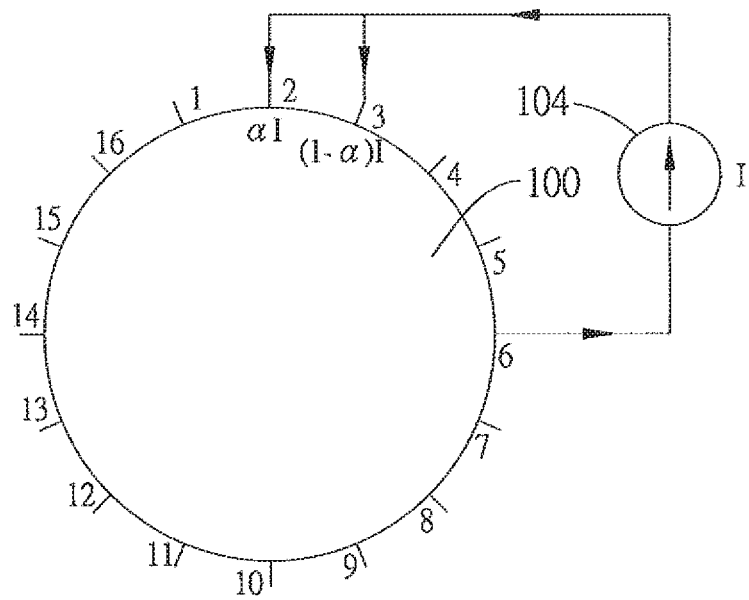
Figure 5C:
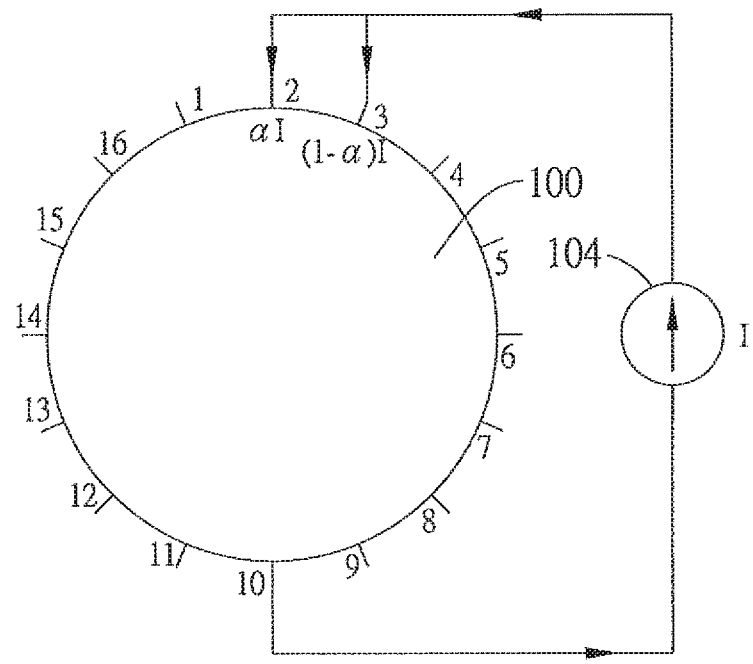

Specifically, in step S21a, the plurality of conducting electrodes may be arranged adjacently, or in different manners on the surrounding of or inside the tissue structure 100, as shown in FIGS. 5A-5C. In FIG. 5A, an electric current is inputted into the tissue structure 100 through the adjacent conducting electrodes 1, 16; and the conducting electrode 3 outputs the electric current. An electric current may also be inputted into the tissue structure 100 through the adjacent conducting electrodes 2, 3; and the conducting electrode 6 outputs the electric current, as shown in FIG. 5B. In addition, FIG. 5C shows that an electric current may also be inputted into the tissue structure 100 through the adjacent conducting electrodes 2, 3; and the conducting electrode 10 outputs the electric current. In an example of the present disclosure, the electric current can be generated by an electric current source 104.

Subsequently, in step S22a, an electric current ratio may be applied to control electric current using an electric current steering device; and a virtual electrode is formed between the at least two of the plurality of the conducting electrodes for inputting electric current.

Figure 5D:
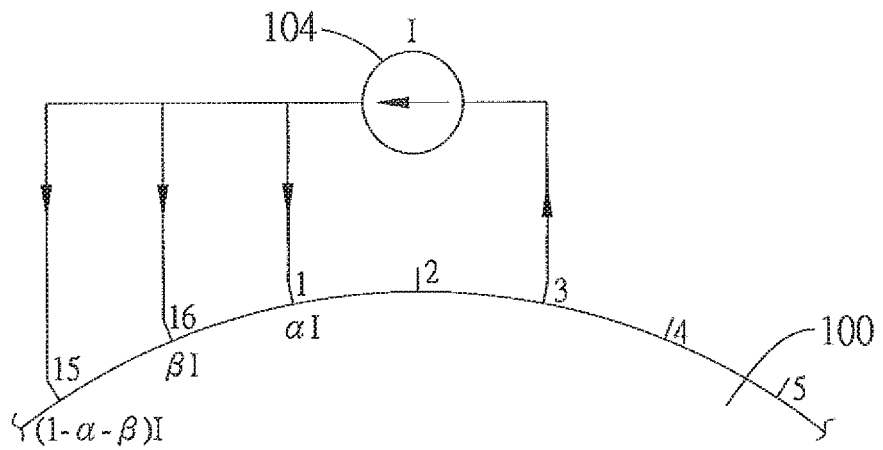

In one example of the present disclosure, the electric current steering device is connected with the electric current source 104; and the electric current ratio may be between 0%-100%. For example, in FIG. 5A, an electric current ratio may be expressed as $\alpha I:(1-\alpha)I$, and is applied to the conducting electrodes 1, 16; wherein I is the electric current source 104 and $\alpha$ is a variable of the electric current ratio. Consequently, a virtual electrode is located between the conducting electrodes 1, 16. In another example of the present disclosure, in FIG. 5B, an electric current ratio may be expressed as $\alpha I:(1-\alpha)I$, and is applied to the conducting electrodes 2, 3. A virtual electrode is located between the conducting electrodes 2, 3. In a further example of the present disclosure, an electric current ratio may also be expressed as $\alpha I:(1-\alpha)I$, and is applied to the conducting electrodes 2, 3. A virtual electrode is also located between the conducting electrodes 2, 3. The electric current ratio may be adjusted; for example, the electric current ratio 50%:50%, or other electric current ratios. Additionally, a virtual electrode is formed between two conducting electrodes which are used for inputting two electric currents based on the electric current ratio. For example, a virtual electrode v is shown in FIG. 5A. For simplicity, the virtual electrode v is shown only in FIG. 5A. Further, if more than two conducting electrodes are used, such as three conducting electrodes, an electric current ratio may be expressed as $\alpha I:\beta I:(1-\alpha-\beta)I$, as shown in FIG. 5D.

In step S23a, an electric potential is measured using at least two of the plurality of conducting electrodes, except these conducting electrodes for inputting and outputting the electric current, to obtain electric current and electric potential distributions corresponding to the plurality of conducting electrodes and the virtual electrodes in the tissue structure 100.

In one embodiment of the present disclosure, the electric current and electric potential distributions corresponding to the plurality of conducting electrodes can be obtained by a signal receiver in order to analyze impedance between the plurality of conducting electrodes.

Afterwards, in step S24a, an image conversion processing is performed to profile an image for a specific region in the tissue structure 100 according to the electric current and electric potential distributions. Moreover, it should be noted that electric current, electric potential and impedance characteristics may be analyzed prior to performing the image conversion processing. The image of the tissue structure can be profiled based on matching the model parameters to the impedance characteristics. In practice, the image conversion processing may be performed by mathematical computing software and model parameters matching; mathematical computing software may be MATLAB. An image with high resolution can be profiled due to sufficient impedance characteristics obtained by a number of virtual electrodes (which are formed between the plurality of conducting electrodes).

Figure 2B:
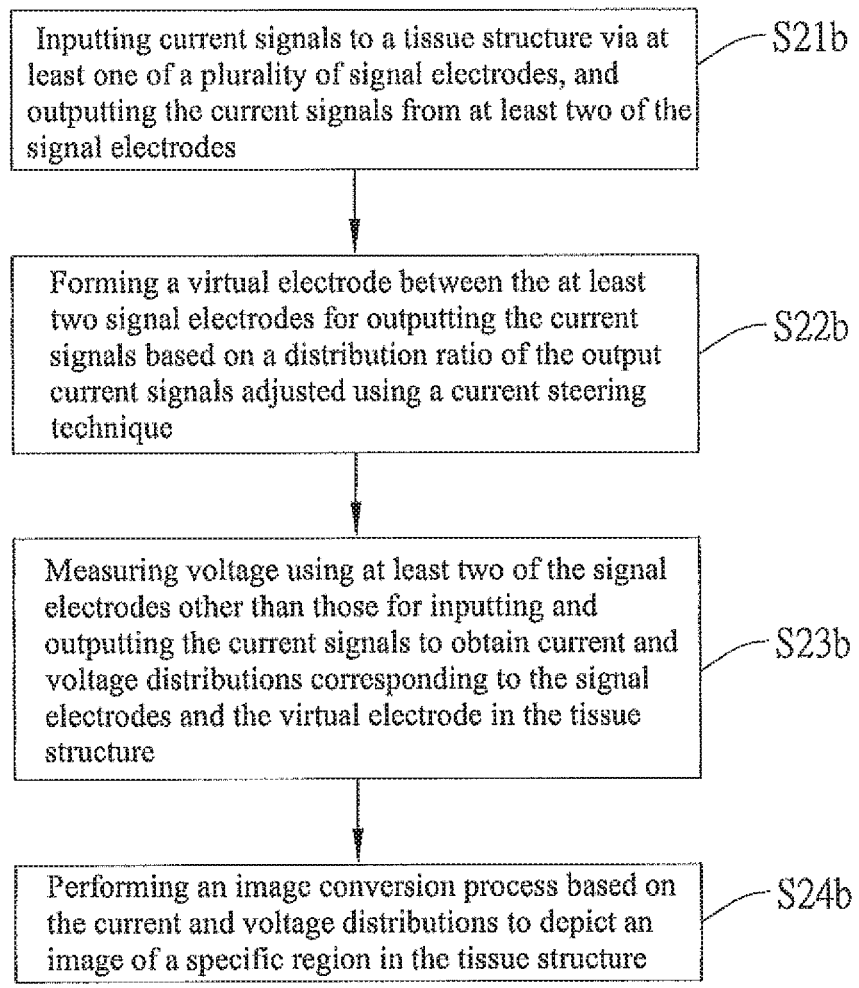
FIG. 2B is a flowchart illustrating a method for improving imaging resolution of EIT according to the second embodiment of the present disclosure.
Figure 6A:
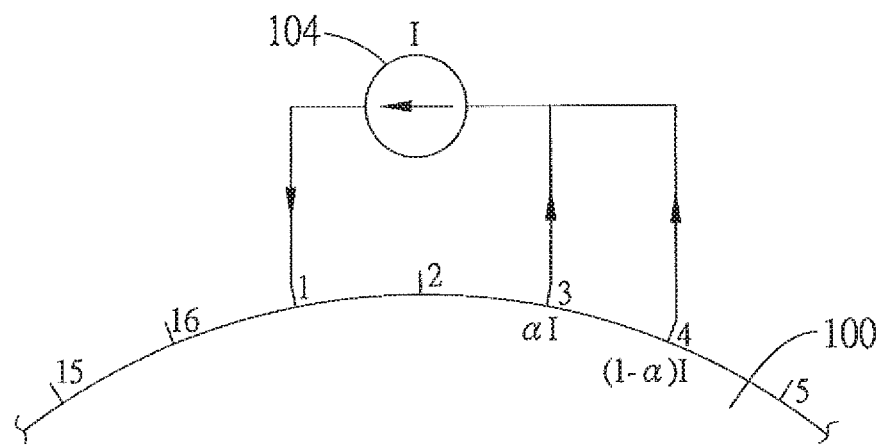
FIGS. 6A-6C are schematic diagrams illustrating a virtual electrode formed between the plurality of conducting electrodes for outputting an electric current by an electric current steering device according to the second embodiment of the present disclosure.
Figure 6B:
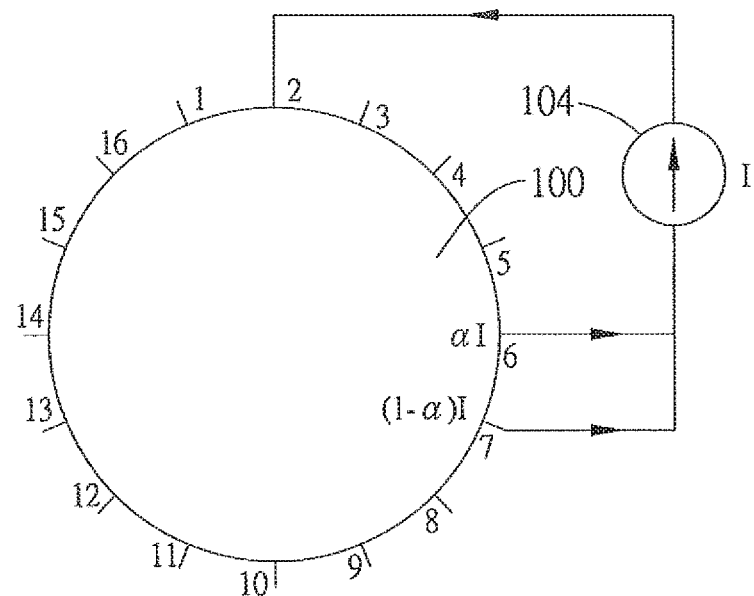
Figure 6C:
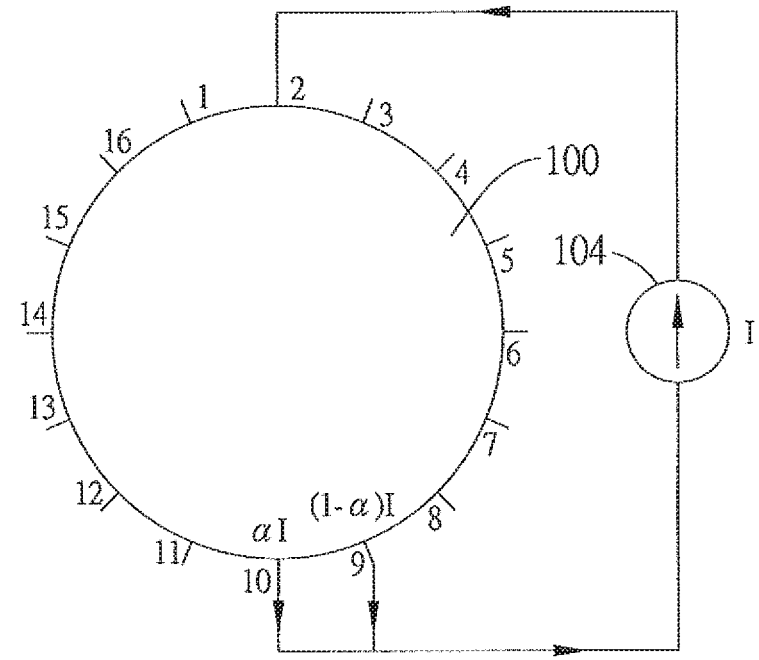

FIG. 2B illustrates a flowchart of the method for improving imaging resolution of EIT according to the second embodiment of the present disclosure. In addition, a virtual electrode is formed between the plurality of conducting electrodes for outputting an electric current by an electric current steering device according to the second embodiment of the present disclosure, as shown in FIGS. 6A-6C.

The method begins with step S21b of inputting an electric current into the tissue structure 100 through at least one of the plurality of conducting electrodes, and outputting the electric current from at least other two of the plurality of conducting electrodes.

In step S22b, an electric current ratio may be applied to control an electric current using an electric current steering device; and a virtual electrode is formed between the at least two of the plurality of the conducting electrodes for outputting electric current.

More specifically, similar to the arrangement of the plurality of conducting electrodes in steps S21a, S22a, the plurality of conducting electrodes may be arranged adjacently, or in different manners on the surrounding of or inside the tissue structure 100. As shown in FIG. 6A, an electric current is inputted into the tissue structure 100 through the conducting electrode 1; and the conducting electrodes 3, 4 output the electric current with an electric current ratio $\alpha I:(1-\alpha)I$. In another example, as shown in FIG. 6B, an electric current is inputted into the conducting electrode 2; and the conducting electrodes 6, 7 output the electric current with an electric current ratio $\alpha I:(1-\alpha)I$. In a further example, as shown in FIG. 6C, an electric current is inputted into the conducting electrode 2; and the conducting electrodes 9, 10 output the electric current with an electric current ratio $\alpha I:(1-\alpha)I$. The electric current ratio $\alpha I:(1-\alpha)I$ may be expressed as $(1-\alpha)I:\alpha I$. Consequently, a virtual electrode may be located in different positions between the conducting electrodes 3, 4, as shown in FIG. 6A, due to varying the variable $\alpha$ of the electric current ratio. Moreover, a virtual electrode may be located in different positions between the conducting electrodes 6, 7, as shown in FIG. 6B, due to varying the variable $\alpha$ of the electric current ratio. As shown in FIG. 6C, a virtual electrode may also be located in different positions between the conducting 9, 10 due to varying the variable $\alpha$ of the electric current ratio.

In step S23b, an electric potential is measured using at least two of the plurality of conducting electrodes, except these conducting electrodes for inputting and outputting the electric current, to obtain electric current and electric potential distributions corresponding to the plurality of conducting electrodes and the virtual electrodes in the tissue structure 100. More specifically, in one example, as shown in FIG. 6A, the conducting electrodes 1 is used for inputting an electric current and the conducting electrodes 3, 4 are used for outputting the electric current, but at least two of the plurality of conducting electrodes not used for inputting or outputting electric current are used for the measurement by a signal receiver. In another example, as shown in FIG. 6B, the conducting electrode 2 is used for inputting an electric current and the conducting electrodes 6, 7 are used for outputting the electric current, but at least two of the plurality of conducting electrodes not used for inputting or outputting electric current are used for the measurement by a signal receiver. In a further example, the conducting electrode 2 is used for inputting an electric current and the conducting electrodes 9, 10 are used for outputting the electric current, but at least two of the plurality of conducting electrodes not used for inputting or outputting electric current are used for the measurement by a signal receiver, as shown in FIG. 6C.

Afterwards, in step S24b, an image conversion processing is performed to profile an image for a specific region in the tissue structure 100 according to the electric current and electric potential distributions. More specifically, the image conversion processing may be performed by mathematical computing software and model parameters matching.

According to the present disclosure, the second embodiment is different from the first embodiment since a virtual electrode is formed between at least two of the plurality of conducting electrodes for outputting the electric current.

Figure 2C:
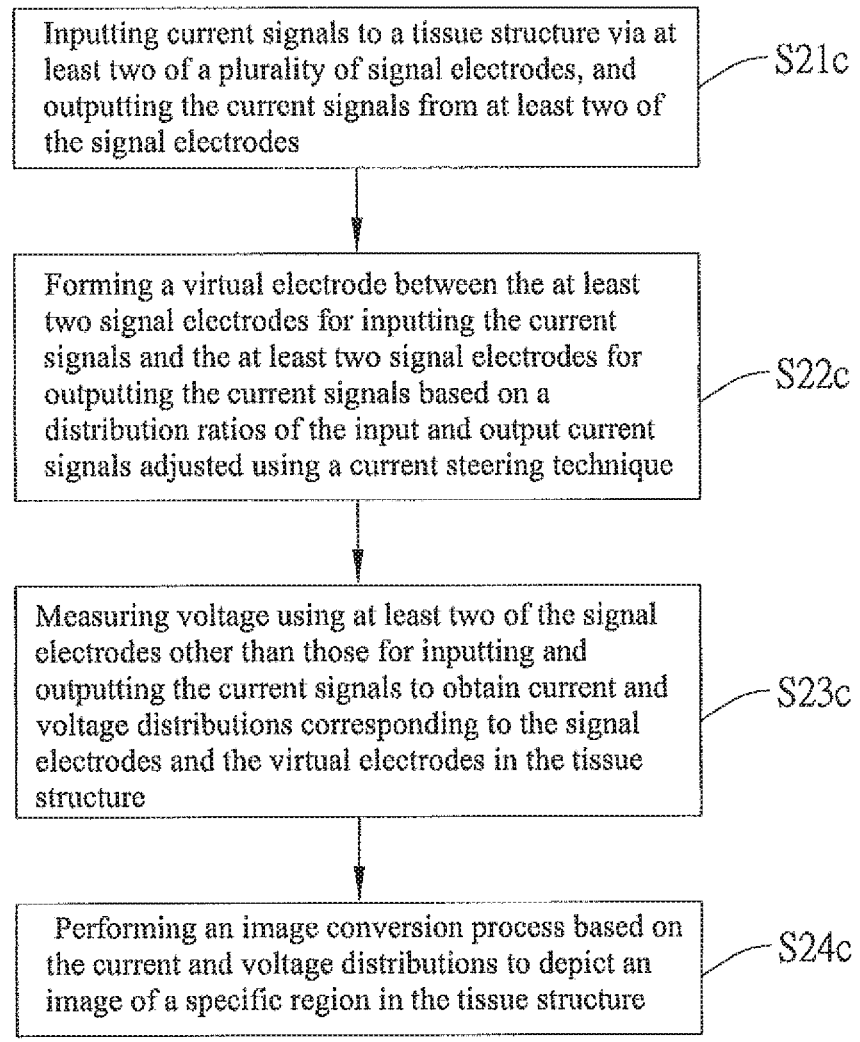
FIG. 2C is a flowchart illustrating a method for improving imaging resolution of EIT according to the third embodiment of the present disclosure.
Figure 7A:
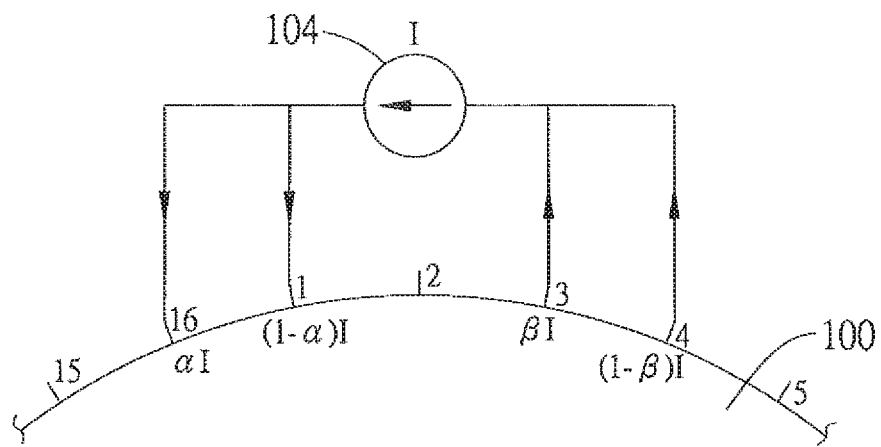
FIGS. 7A-7D are schematic diagrams illustrating virtual electrodes formed between the plurality of conducting electrodes for both inputting and outputting an electric current by an electric current steering device according to the third embodiment of the present disclosure.
Figure 7B:
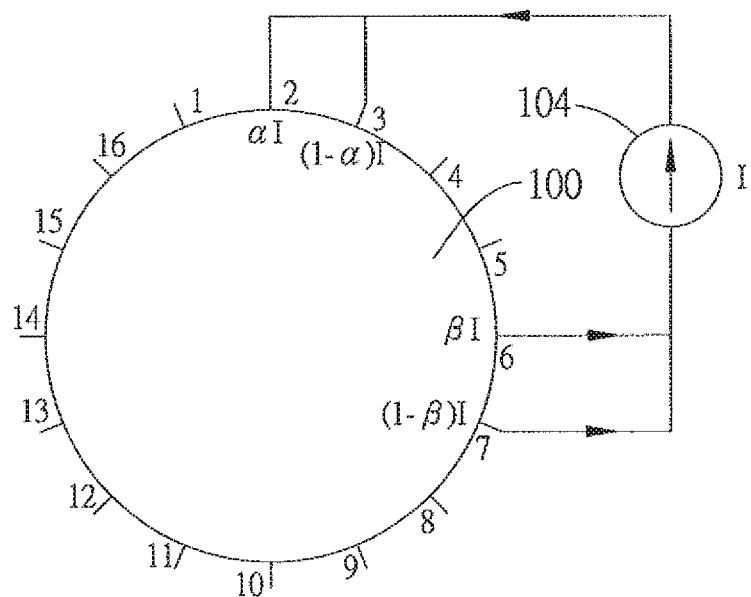
Figure 7C:
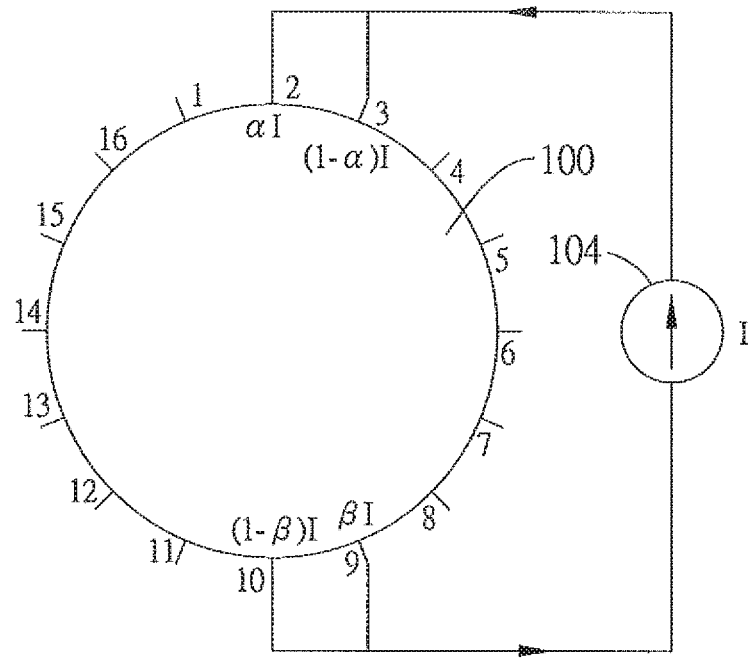

FIG. 2C shows a method for improving imaging resolution of EIT using a plurality of conducting electrodes on the surrounding of or inside a tissue structure. In addition, FIGS. 7A-7C show that a virtual electrode is formed between the plurality of conducting electrodes for inputting an electric current by an electric current steering device according to the third embodiment of the present disclosure.

The method begins with step S21c of inputting an electric current into the tissue structure 100 through at least two of the plurality of conducting electrodes, and outputting the electric current from at least other two of the plurality of conducting electrodes.

In step S22c, an electric current ratio may be applied to control an electric current using an electric current steering device; and a virtual electrode is formed between the at least two of the plurality of conducting electrodes for inputting electric current and another virtual electrode is also formed between the at least two of the plurality of conducting electrodes for outputting electric current.

Specifically, in steps S21c, S22c, the plurality of conducting electrodes may be arranged adjacently, or in different manners on the surrounding of or inside the tissue structure 100. As shown in FIG. 7A, an electric current divided in the electric current ratio $\alpha I:(1-\alpha)I$ is inputted into the tissue structure through the conducting electrodes 1, 16; and the conducting electrodes 3, 4 output the electric current in the electric current ratio $\beta I:(1-\beta)I$. Consequently, a virtual electrode is formed between the conducting electrodes 1, 16; and another virtual electrode is formed between the conducting electrodes 3, 4. In another example, as shown in FIG. 7B, an electric current divided in the electric current ratio $\alpha I:(1-\alpha)I$ is inputted into the tissue structure through the conducting electrodes 2, 3; and the conducting electrodes 6, 7 output the electric current in the electric current ratio $\beta I:(1-\beta)I$. In a further example, as shown in FIG. 7C, an electric current divided in the electric current ratio $\alpha I:(1-\alpha)I$ is inputted into the tissue structure through the conducting electrodes 2, 3; and the conducting electrodes 9, 10 output the electric current in the electric current ratio $\beta I:(1-\beta)I$. The input electric current ratio can be expressed as $\alpha I:(1-\alpha)I$ or $(1-\alpha)I:\alpha I$; and the output electric current ratio can be expressed as $\beta I:(1-\beta)I$ or $(1-\beta)I:\beta I$. The value of the variable $\alpha$ can be the same as the value of the variable $\beta$, or different from the value of the variable $\beta$. Moreover, a virtual electrode may be located in different positions between the conducting electrodes 1, 16; and another virtual electrode may also be located in different positions between the conducting electrodes 3, 4 due to varying the variables $\alpha$, $\beta$, as shown in FIG. 7A. As shown in FIG. 7B, a virtual electrode may be located in different positions between the conducting electrodes 2, 3; and another virtual electrode may also be located in different positions between the conducting electrodes 6, 7 due to varying the variables $\alpha$, $\beta$. In addition, as shown in FIG. 7C, a virtual electrode may be located in different positions between the conducting electrodes 2, 3; and another virtual electrode may also be located in different positions between the conducting electrodes 9, 10 due to varying the variables $\alpha$, $\beta$.

In step S23c, an electric potential is measured using at least two of the plurality of conducting structures, except theses conducting electrodes for inputting and outputting the electric current, to obtain electric current and electric potential distributions corresponding to the plurality of conducting electrodes and the virtual electrodes in the tissue structure 100. More specifically, in one example, as shown in FIG. 7A, the conducting electrodes 1, 16 are used for inputting an electric current and the conducting electrodes 3, 4 are used for outputting the electric current, but at least two of the plurality of conducting electrodes not used for inputting or outputting electric current are used for the measurement by a signal receiver. In another example, as shown in FIG. 7B, the conducting electrodes 2, 3 are used for inputting an electric current and the conducting electrodes 6, 7 are used for outputting the electric current, but at least two of the plurality of conducting electrodes not used for inputting or outputting electric current are used for the measurement by a signal receiver. In a further example, the conducting electrodes 2, 3 are used for inputting an electric current and the conducting electrodes 9, 10 are used for outputting the electric current, but at least two of the plurality of conducting electrodes not used for inputting or outputting electric current are used for the measurement by a signal receiver.

Afterwards, in step S24c, an image conversion processing is performed to profile an image for a specific region in the tissue structure 100 according to the electric current and electric potential distributions. More specifically, the image conversion processing may be performed by mathematical computing software and model parameters matching.

Figure 7D:
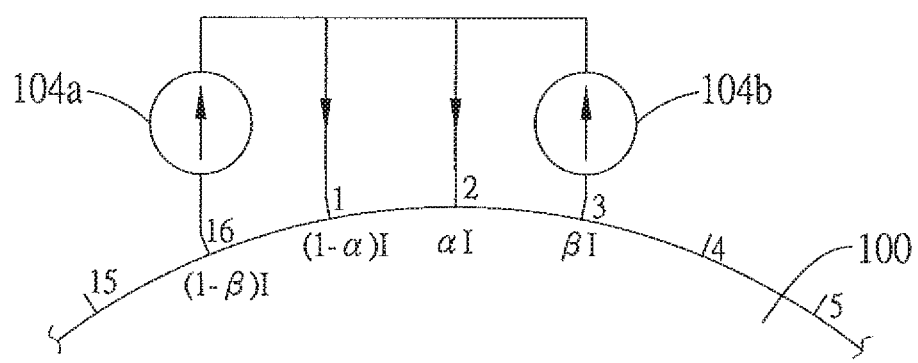

Accordingly, according to the third embodiment of the present disclosure, an electric current divided in the electric current ratio $(1-\alpha)I:\alpha I$ is inputted into the tissue structure through the conducting electrodes 1, 2; and the conducting electrodes 16, 3 output the electric current in the electric current ratio $(1-\beta)I:\beta I$ as shown in FIG. 7D. A virtual electrode may be located in any positions between the conducting electrodes 1, 2 to increase accuracy of the position of the virtual electrode.

It can be seen that the third embodiment of the present disclosure is different from the first and the second embodiments since a virtual electrode is formed between at least two of the plurality of conducting electrodes for inputting an electric current; and another virtual electrode is also formed between at least two of the plurality of conducting electrodes for outputting the electric current.

Further, the present disclosure can be more fully understood by reading the following detailed description with reference made to the accompanying drawings.

Figure 3:
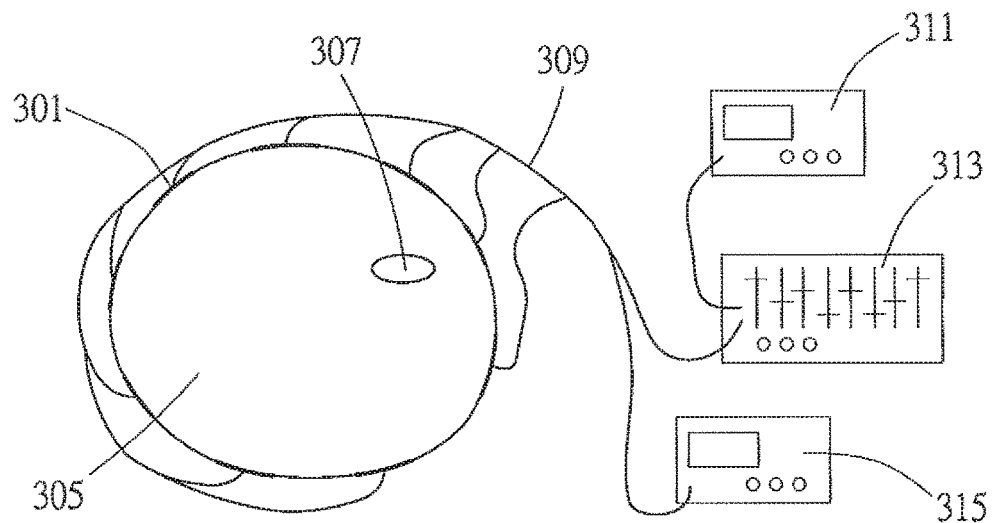
FIG. 3 is a cross sectional diagram depicting a plurality of conducting electrodes attached to the surrounding of a tissue structure according to the present disclosure.
Figure 4:
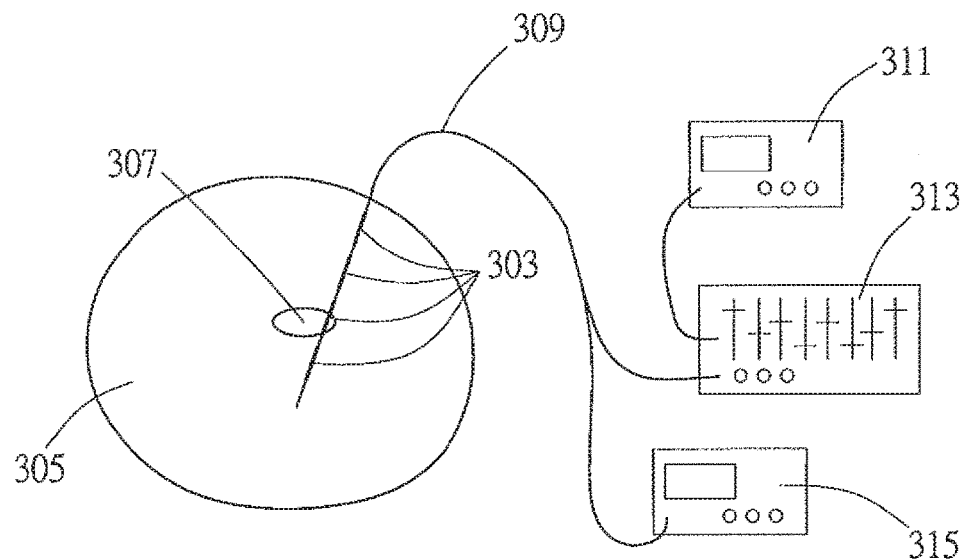
FIG. 4 is a cross sectional diagram depicting a composite probe with a plurality of conducting electrodes forming an electrode array inserted in a tissue structure according to the present disclosure.

FIG. 3 shows a cross sectional diagram depicting a plurality of conducting electrodes 301 attached to the surrounding of a tissue structure 305 according to the present disclosure. FIG. 4 shows a cross sectional diagram depicting a composite probe with a plurality of conducting electrodes 303 forming an electrode array inserted in the tissue structure 305 according to the present disclosure;

As shown in FIG. 3, the plurality of conducting electrodes 301 is attached to the surrounding of the tissue structure 305. A specific region 307 is located inside the tissue structure 305. An integrated wire 309 connects a plurality of conducting electrodes 301 to a signal generator 311 (as an electric current source), an electric current steering device 313 (as an electric current ratio controller) and a signal receiver 315 (for measuring an electric potential). At least two of the plurality of conducting electrodes 301 are used for inputting or outputting an electric current according to the first, the second and the third embodiments of the present disclosure. Certainly, the plurality of conducting electrodes used for inputting or outputting an electric current, or measuring an electric potential may be varied according to various different measurements.

Furthermore, as shown in FIG. 4, in one embodiment of the present disclosure, a composite probe with a plurality of conducting electrodes 303 arranged in an electrode array inserted in a tissue structure 305. A specific region 307 is located inside the tissue structure 305. An integrated wired 309 connects the composite probe to a signal generator 311 (as an electric current source), an electric current steering device 313 (as an electric current ratio controller) and a signal receiver 315 (for measuring an electric potential). At least two of the plurality of conducting electrodes 303 within the composite probe are used for inputting or outputting an electric current according to the first, the second and the third embodiments of the present disclosure. The plurality of conducting electrodes of the composite probe used for inputting or outputting an electric current or measuring electric potential may be varied according to various different measurements.

Any image reconstruction method can be applied to the image conversion processing of the present disclosure, selectively uses discrete vector data by measuring discrete values from conducting electrodes. For example, for N conducting electrodes, $N(N-1)/2$ independent boundary measurements are required (if some input conducting electrodes are not used, the number of measurements will be less than this). The reconstructed image will include a set of discrete pixels, and two sets of measurements may easily represent through matrix transformation, the relationship between the vector of the transfer impedance z and the image vector of the conductivity c, as indicated by formula (1): $z=T(c)c$. More specifically, transfer impedance is the measured electric potential divided by the applied electric current between a pair of conducting electrodes (or between a conducting electrode and a normal reference point). Generally, a matrix T depends on the distribution of the conductivity and the applied electric current or electric potential. The distribution of the conductivity can be computed using the improved Newton-Raphson method. In the kth stage, that is, in the iteration process, the conductivity related to the boundary electric potential can be obtained by formula (2): $v=F(c)$.

Then, based on formula (3): $c^{k+1}=c^k+\Delta c$, an estimation of the $(k+1)^{th}$ conductivity can be computed, wherein $\Delta c=\{[F'(c^k)]'F'(c^k)\}^{-1}F'(c^k)[F(c^k)-v_0]$, and $v_0$ is the Jacobian matrix $[F']_{ij}=df_i/d_j$ of the measure electric potential and $F'(C^K)$. The above algorithm provides a good initial estimation of the conductivity, and ensures a sufficient convergence. In addition, the above algorithm can actually be applied using highly efficient finite elements to calculate forward transformation and direct differentiation of the Jacobian matrix mainly involving the inverse matrix of $\{[F'(c^k)]'F'(c^k)\}$ and the essential normalization technique, which are not further described herein.

In addition, the method for improving imaging resolution of EIT can further be applied to other related fields, such as deep brain stimulation, spinal cord stimulation, vagus nerve stimulation, cochlear implants, retinal prosthesis, breast cancer detection and lung ventilation monitor. In other words, the abovementioned tissue structure may be a brain, cochlea, spinal cord, a neck region or a chest region.

Figure 1A:
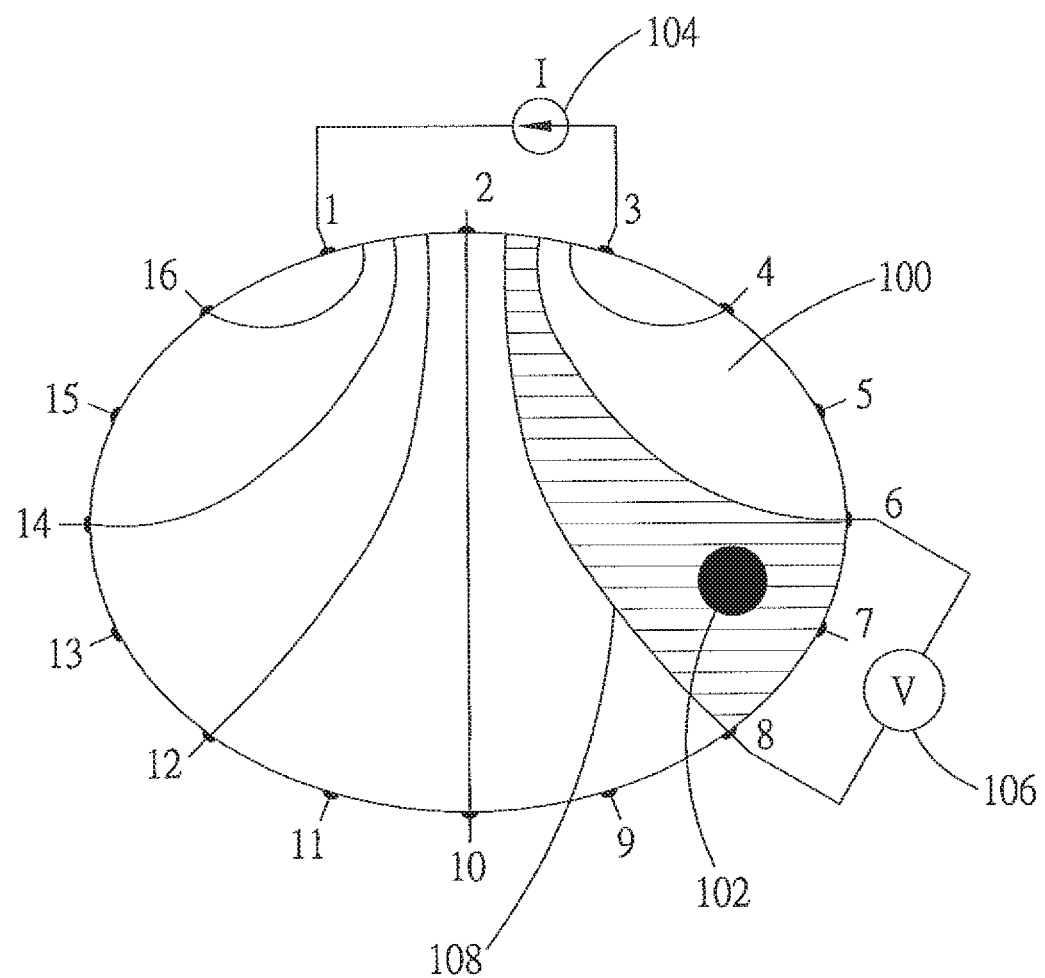
FIGS. 1A-1C are 2D schematic diagrams depicting the existing electrical impedance tomography (EIT) techniques.
Figure 1B:
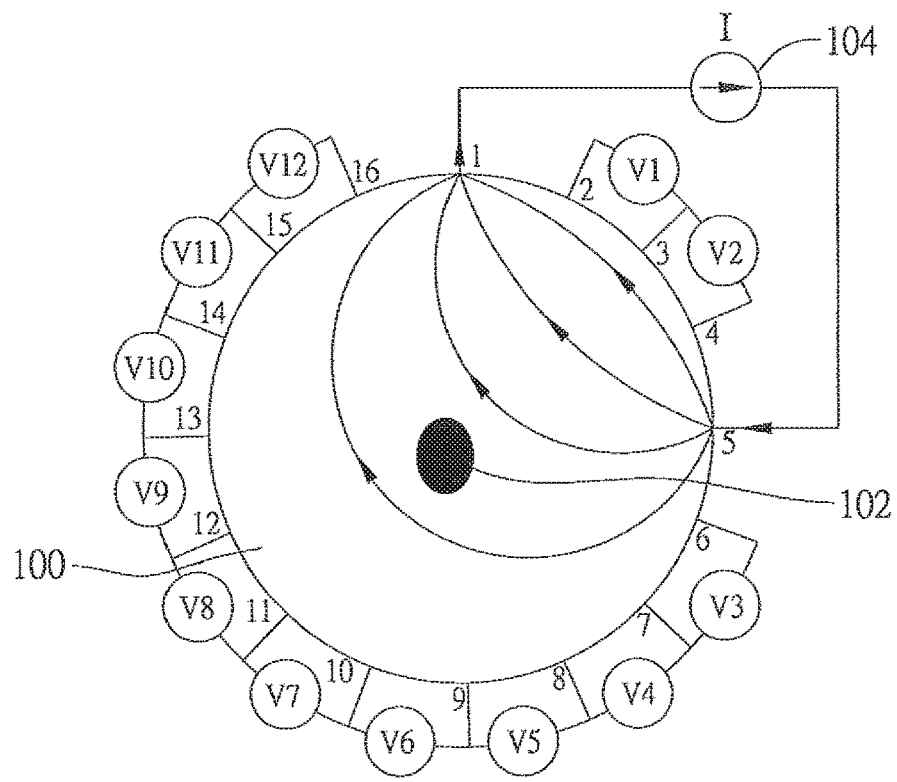
Figure 1C:
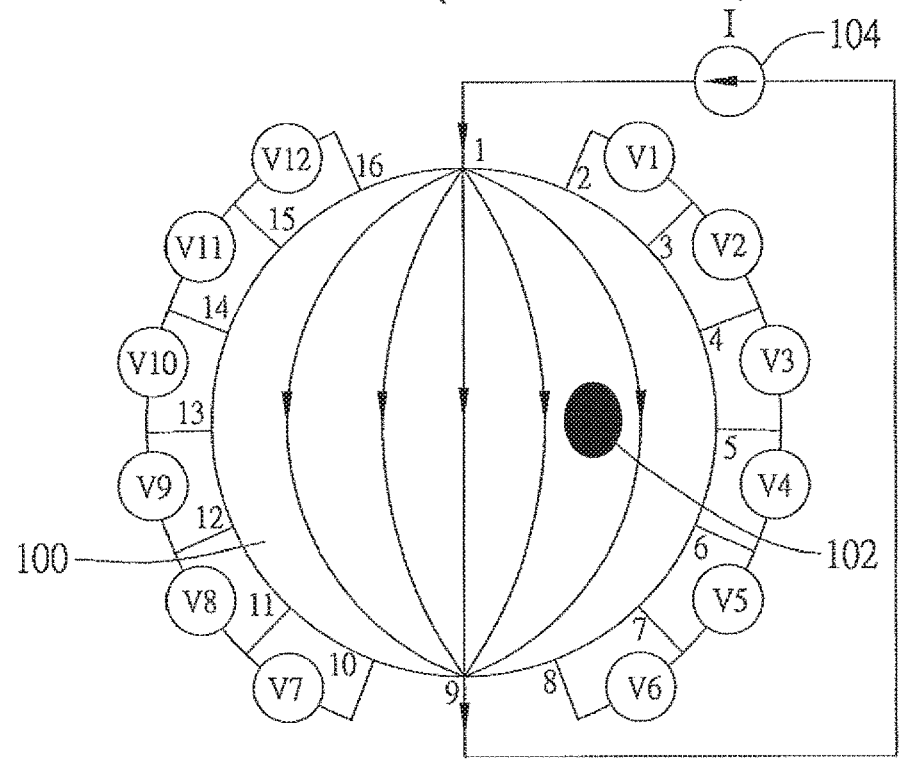

Besides, the current EIT technology can also be applied prior to performing steps S21a, S21b, S21c. More specifically, measurements of the electric potential may be performed prior to performing steps S21a, S21b, S21c, according to FIG. 1A, 1B or 1C of the present disclosure. Then, the subsequent measurements can be completed based on virtual electrodes formed, according to the method of the present disclosure. Consequently, an EIT image with high resolution and accuracy can be improved.

Moreover, the present disclosure further provides a 3D EIT system. A schematic diagram illustrating virtual electrodes formed between the plurality of conducting electrodes is shown in FIG. 8A, according to the 3D EIT system of the present disclosure.

Figure 8A:
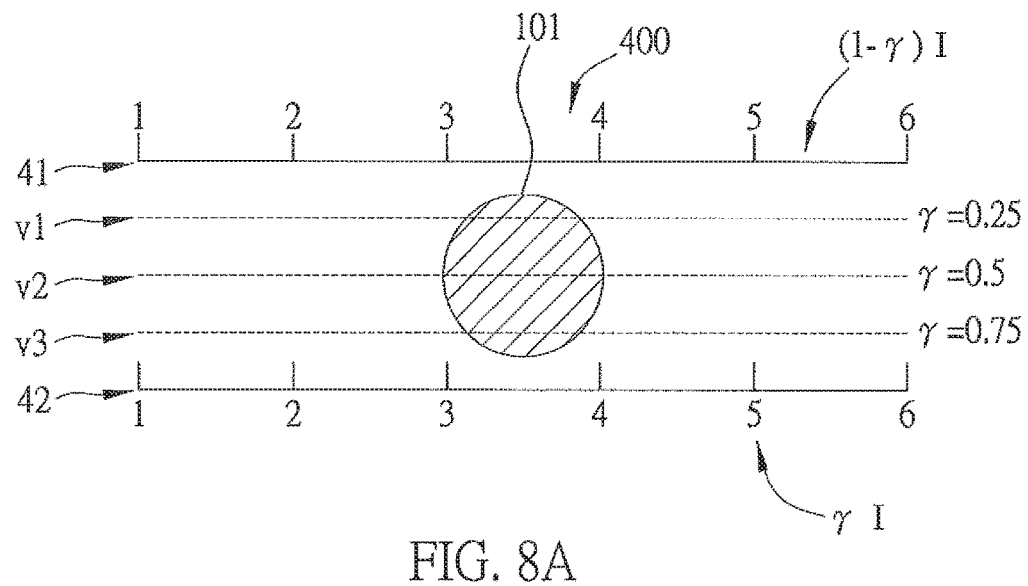
FIG. 8A is a schematic diagram illustrating virtual electrodes formed between the plurality of conducting electrodes according to one of the embodiments of the 3D EIT system of the present disclosure.

In one embodiment, as shown in FIG. 8A, the 3D EIT system 400 comprises a plurality of conducting electrode devices, such as two conducting electrode devices 41, 42, of which each conducting device has a plurality of conducting electrodes, such as six conducting electrodes 1-6; a tissue structure 101 is located between the plurality of conducting electrode devices 41, 42. More specifically, the plurality of conducting electrode devices comprises the plurality of conducting electrodes in a ring manner.

Figure 8B:
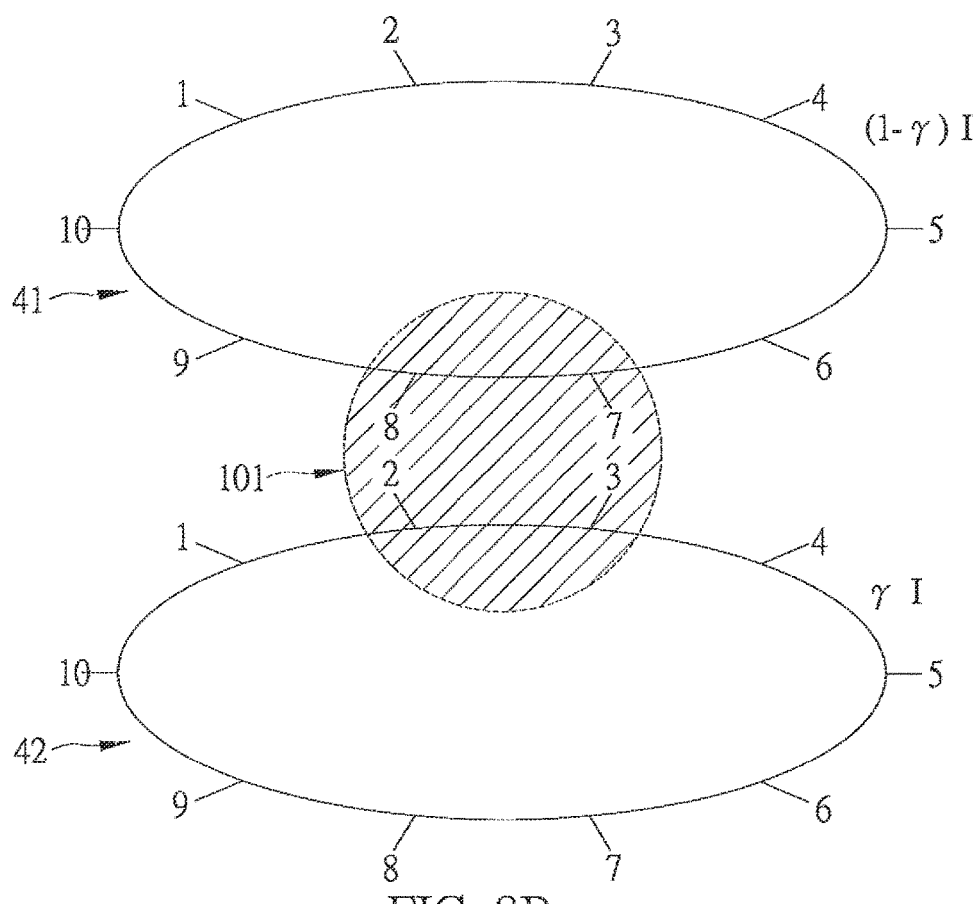
FIG. 8B is a schematic diagram illustrating the 3D EIT system according to one embodiment of the present disclosure.

Referring to FIG. 8B, a schematic diagram of the 3D EIT system is illustrated according to the present disclosure. The tissue structure 101 is located between the plurality of conducting electrode devices 41, 42. Each electrode device or 2D electrode array consists of electrode 1-10, as shown in FIG. 8B, and can be considered as similar to FIG. 1A. An electric current divided in the electric current ratio $(1-\gamma)I:\gamma I$ is inputted into the tissue structure by the conducting electrode devices 41, 42.

In other words, an electric current $(1-\gamma)I$ is inputted into the tissue structure by the conducting electrode device 41 while another electric current $\gamma I$ is also inputted into the tissue structure by the conducting electrode device 42. In addition, a virtual electrode device is located between the conducting electrode devices according to the electric current ratio. For example, as shown in FIG. 8A, a virtual electrode device v2 is located in the middle of the conducting electrode devices 41, 42 while the value of the variable $\gamma$ is 0.5. In another example, as shown in FIG. 8A, a virtual electrode device v1 is located in the upper quarter between the conducting electrode devices 41, 42 while the value of the variable $\gamma$ is 0.25. In a further example, as shown in FIG.

8A, a virtual electrode device v3 is located in the lower quarter between the conducting electrode devices 41, 42.

Referring to FIG. 8A, an image of the specific region in the tissue structure 101 is profiled by the conducting electrode devices 41, 42. More specifically, five images of the tissue structure 101 can be profiled by the virtual electrode devices v1, v2, v3 and the conducting electrode devices 41, 42 based on three different electric current ratios, as shown in the 3D EIT system of FIG. 8A.

Subsequently referring to FIG. 8C, a schematic diagram of a 3D EIT system is illustrated according to another embodiment of the present disclosure. A 3D EIT system having four conducting electrode devices or four layers of 2D electrode array 41, 42, 43, 44 is provided. Four 2D EIT images can be obtained by the four conducting electrode devices or four layers of 2D electrode array 41, 42, 43, 44. In addition, nine 2D EIT images can be obtained by three pairs of neighboring electrode devices (41 and 42, 42 and 43, 43 and 44), while the values of the variable γ are set to be 0.25, 0.5 and 0.75. Therefore, a 3D EIT image of the tissue structure 101 can be obtained based on the thirteen EIT images of the tissue structure 101.

A 3D EIT image of the tissue structure 101 can further be obtained based on the thirty EIT images of the tissue structure 101, which is completed by the conducting electrode devices or layers of electrode arrays 41, 42, 43, 44 while the values of the variable γ are set to be 0, 0.1, 0.2, 0.3, 0.4, 0.5, 0.6, 0.7, 0.8, 0.9 and 1.

Figure 8C:
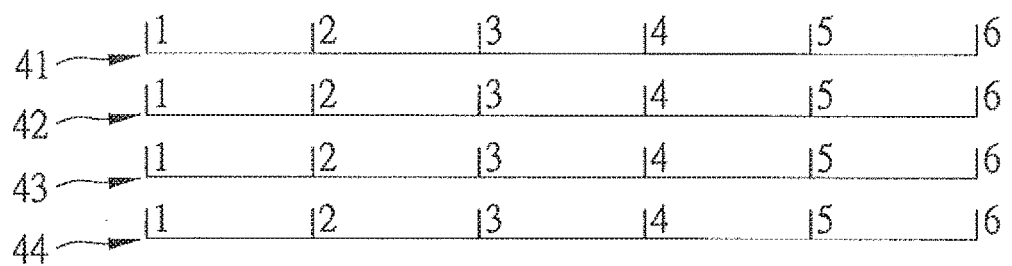
FIG. 8C is a schematic diagram illustrating the 3D EIT system according to another embodiment of the present disclosure.

Accordingly, referring to FIGS. 8A-8C, the conducting electrode devices may be arranged adjacently or in different manners on the surrounding of or inside the tissue structure. A 3D EIT image can be obtained by the plurality of 2D images based on adjusting an electric current divided in different electric current ratios.

Consequently, current steering techniques, as illustrated from FIGS. 1-7, can be applied to set up with multiple levels 2D electrode arrays (as illustrated in FIG. 8C) in order to generate 3D EIT images.

Two other imaging techniques are also available for imaging the biological tissue structure, such as electrical resistivity tomography (ERT) and electrical resistivity imaging (ERI) except EIT. ERI is a technique for imaging surface structures from impedance measurements made by conducting electrodes, similar to EIT. In addition, electrical capacitance tomography (ECT) is another imaging technique for dielectric permittivity measurements. Imaging resolution of ERT or ECT can be improved by an electric current steering technique. ERT and ECT may be applied to pipe fluid flow monitoring, imaging/monitoring underground, or imaging/monitoring fluid flow inside pipes. According to the embodiments of the present disclosure, the electric current steering technique is incorporated with EIT in order to enhance imaging resolution of the 3D EIT system. The electric potential distribution and electric current flow can be adjusted by the electric current steering technique. Moreover, a specific area in the body can be observed with high resolution without physically increasing the number of conducting electrodes. In other words, a virtual electrode is formed between at least two of the plurality of conducting electrodes by applying the electric current ratio to control electric current using an electric current steering device. An electric potential using at least two of the plurality of conducting electrodes, except these conducting electrodes for inputting and outputting electric current, to obtain electric current and electric potential distributions corresponding to the plurality of conducting electrodes and the virtual electrode in the tissue structure. Imaging conversion processing is performed according to the electric current and electric potential distributions to profile an image for the specific region in the tissue structure.

Further, regarding the applications of ERT, ERT can be applied to interface detection. For example, ERT can be used in the interface detection between fluid and solid, and also includes shape detection of the interface between fluid and solid.

In process imaging, the induced polarization method can be used in a similar fashion to EIT or ERT, and is a geophysical imaging technique used to identify subsurface materials, in that an electric current is induced into the subsurface through two electrodes, and an electric potential is monitored through two other electrodes.

In summary, the present disclosure provides a method for improving imaging resolution of EIT. A number of virtual electrodes are formed between finite conducting electrodes using the electric current steering technique. Subsequently, the image conversion processing can be performed based on the electric current and electric potential distributions obtained through the number of virtual electrodes and the finite conducting electrodes. Consequently, imaging resolution and accuracy of EIT is improved rapidly. Therefore, the technical issue that the current EIT only has finite conducting electrodes is solved by forming a number of virtual electrodes. Accordingly, imaging resolution of EIT is improved without repeating the process for numerous different configurations of applied electric current.

The above embodiments are only used to illustrate the principles of the present disclosure, and they should not be construed as to limit the present disclosure in any way. The above embodiments can be modified by those with ordinary skill in the art without departing from the scope of the present disclosure as defined in the following appended claims.

What is claimed is:

1. A 3D electrical impedance tomography (EIT) system, comprising:
   an electric current source;
   an electric current steering device;
   a signal receiver for measuring an electric potential;
   a plurality of conducting electrodes surrounding or inside a tissue structure;
   integrated wires connecting the plurality of conducting electrodes, the electric current source, the electric current steering device and the signal receiver;
   wherein the electric steering device is programmed to:
   (1) input an electric current, by the electric current source, into the tissue structure through at least two of the plurality of conducting electrodes, and output the electric current from at least an other one of the plurality of conducting electrodes;
   (2) adjust an electric current ratio of the inputted electric current according to the electric current steering device connected to the electric current source to form a virtual electrode between the at least two of the plurality of conducting electrodes, wherein the virtual electrode is located between the at least two of the plurality of conducting electrodes corresponding to the electric current ratio for inputting the electric current;
   (3) measure an electric potential using the at least two of the plurality of conducting electrodes, except these conducting electrodes for inputting and outputting the electric current, to obtain electric current and electric potential distributions corresponding to the plurality of conducting electrodes and the virtual electrode in the tissue structure; and
(4) perform an image conversion processing according to the electric current and electric potential distributions to profile an image for a specific region in the tissue structure.

2. The system of claim 1, wherein the plurality of conducting electrodes are disposed in a ring manner.

3. The system of claim 1, wherein the electric current ratio is between 0%-100%.

4. The system of claim 1, wherein the plurality of conducting electrodes are microelectrodes which are formed into an electrode array.

5. The system of claim 1, wherein the tissue structure is a brain, cochlea, spinal cord, a neck region or a chest region.

6. The system of claim 1, wherein a relation between the electric current ratio and the electric current is expressed as $\alpha I:(1-\alpha)I$, wherein I is the electric current and $\alpha$ is the electric current ratio for inputting the electric current, and wherein $0 \leq \alpha \leq 1$.

7. The system of claim 1, wherein a relation between the electric current ration and the electric current is expressed as $\alpha I:\beta I:(1-\alpha-\beta)I$, wherein I is the electric current, $\alpha$ and $\beta$ are the electric current ratios for inputting the electric current, and wherein $0 \leq \alpha \leq 1$ and $0 \leq \beta \leq 1$.

8. A 3D electrical impedance tomography (EIT) system, comprising:
an electric current source;
an electric current steering device;
a signal receiver for measuring an electric potential;
a plurality of conducting electrodes surrounding or inside a tissue structure;
integrated wires connecting the plurality of conducting electrodes, the electric current source, the electric current steering device and the signal receiver;
wherein the electric steering device is programmed to:
(1) input an electric current, by the electric current source, into the tissue structure through at least one of the plurality of conducting electrodes, and output the electric current from at least an other one of the plurality of conducting electrodes;
(2) adjust an electric current ratio of the outputted electric current according to the electric current steering device connected to the electric current source to form a virtual electrode between the at least other two of the plurality of conducting electrodes, wherein the virtual electrode is located between the at least other two of the plurality of conducting electrodes corresponding to the electric current ratio for outputting the electric current;
(3) measure an electric potential using the at least two of the plurality of conducting electrodes, except these conducting electrodes for inputting and outputting the electric current, to obtain electric current and electric potential distributions corresponding to the plurality of conducting electrodes and the virtual electrode in the tissue structure; and
(4) perform an image conversion processing according to the electric current and electric potential distributions to profile an image for a specific region in the tissue structure.

9. The system of claim 8, wherein the plurality of conducting electrodes are disposed in a ring manner.

10. The system of claim 8, wherein the electric current ratio is between 0%-100%.

11. The system of claim 8, wherein the plurality of conducting electrodes are microelectrodes which are formed into an electrode array.

12. The system of claim 8, wherein the tissue structure is a brain, cochlea, spinal cord, a neck region or a chest region.

13. The system of claim 8, wherein a relation between the electric current ratio and the electric current is expressed as $\alpha I:(1-\alpha)I$, wherein I is the electric current and $\alpha$ is the electric current ratio for outputting the electric current, and wherein $0 \leq \alpha \leq$.

14. The system of claim 8, wherein a relation between the electric current ration and the electric current is expressed as $\alpha I:\beta I:(1-\alpha-\beta)I$, wherein I is the electric current, $\alpha$ and $\beta$ are the electric current ratios for outputting the electric current, and wherein $0 \leq \alpha \leq 1$ and $0 \leq \beta \leq 1$.

15. A 3D electrical impedance tomography (EIT) system, comprising:
an electric current source;
an electric current steering device;
a signal receiver for measuring an electric potential;
a plurality of conducting electrodes surrounding or inside a tissue structure;
integrated wires connecting the plurality of conducting electrodes, the electric current source, the electric current steering device and the signal receiver;
wherein the electric steering device is programmed to:
(1) input an electric current, by the electric current source, into the tissue structure through at least two of the plurality of conducting electrodes, and output the electric current from at least an other one of the plurality of conducting electrodes;
(2) adjust at least two electric current ratios of the inputted and the outputted electric currents according to the electric current steering device connected to the electric current source to form at least two virtual electrodes between the at least two of the plurality of conducting electrodes, wherein the virtual electrodes are located between the at least two of the plurality of conducting electrodes corresponding to the electric current ratio for inputting the electric current and between the at least other two of the conducting electrodes for outputting the electric current;
(3) measure an electric potential using the at least two of the plurality of conducting electrodes, except these conducting electrodes for inputting and outputting the electric current, to obtain electric current and electric potential distributions corresponding to the plurality of conducting electrodes and the virtual electrodes in the tissue structure; and
(4) perform an image conversion processing according to the electric current and electric potential distributions to profile an image for a specific region in the tissue structure.

16. The system of claim 15, wherein the plurality of conducting electrodes are disposed in a ring manner.

17. The system of claim 15, wherein the electric current ratios are between 0%-100%.

18. The system of claim 15, wherein the plurality of conducting electrodes are microelectrodes which are formed into an electrode array.

19. The system of claim 15, wherein the tissue structure is a brain, cochlea, spinal cord, a neck region or a chest region.

20. The system of claim 15, wherein relations between the electric current ratio and the electric current are expressed as $\alpha I:(1-\alpha)I$ and $\beta I:(1-\beta)I$, wherein I is the electric current, $\alpha$ is the electric current ratio for inputting the electric current and $\beta$ is the electric current ratio for outputting the electric current, and wherein $0 \leq \alpha \leq 1$ and $0 \leq \beta \leq 1$.

\* \* \* \* \*